United States Patent [19]

Lovick

[11] 4,076,020

[45] Feb. 28, 1978

[54] VETERINARY APPLIANCE

[76] Inventor: James S. Lovick, Rte. 2, Box 76-B, Henderson, Tex. 75652

[21] Appl. No.: 748,067

[22] Filed: Dec. 6, 1976

[51] Int. Cl.[2] .......... A61F 5/24

[52] U.S. Cl. .......... 128/98; 128/157; 128/268

[58] Field of Search .......... 128/127, 98, 157, 327, 128/132 R, 268

[56] References Cited

U.S. PATENT DOCUMENTS

| | | | |
|---|---|---|---|
| 2,606,552 | 8/1952 | Payton | 128/98 |
| 2,825,330 | 3/1958 | Storz | 128/98 |
| 4,026,290 | 5/1977 | Brooker et al. | 128/268 |
| 4,036,229 | 7/1977 | Marinello | 128/268 |

*Primary Examiner*—Lawrence W. Trapp
*Attorney, Agent, or Firm*—Hubbard, Thurman, Turner, Tucker & Glaser

[57] ABSTRACT

A veterinary appliance useful for treatment of edematous tissue, such as an edematous prolapsed bovine cervix, includes a flexible band member adapted to fit around the edematous tissue. One end of the band member is affixed to a housing and the other end is operably connected to a roller that is rotatably supported by the housing. Rotation of the roller in a predetermined direction will cause the effective length of the band member to thereby cause an even squeezing pressure to the edematous tissue.

7 Claims, 6 Drawing Figures

VETERINARY APPLIANCE

BACKGROUND OF THE INVENTION

This invention relates to an improved veterinary appliance. In another aspect, this invention relates to an improved veterinary appliance that is used in the treatment of edematous animal tissue. In still another aspect, this invention relates to an improved veterinary appliance that is useful in the size reduction of an edematous prolapsed bovine cervix.

It is well known in the field of veterinary medicine that the involuntary extrusion of certain organs and tissue from certain animals, such as bovine females, is common. One particular troublesome and common malady experienced by female bovine animals is a condition known as a prolapsed bovine cervix, wherein the tissue forming and surrounding the bovine cervix is displaced and is extruded through the vagina of the animal. In most instances where the prolapsed cervix condition exists in bovine animals, the condition is very quickly aggravated due to the fact that such tissue and organs are very sensitive, especially in a harsh environment such as is experienced when the tissue and organs are extruded from the body of the animal. Thus, the tissue becomes irritated and inflamed and almost immediately begins to swell. As the prolapsed cervix is exposed to the harsh environment outside the animal, an edematous condition rapidly develops with the prolapsed cervix becoming swollen and inflamed.

As the edematous prolapsed bovine cervix is exposed to dirt, insects and other foreign bodies, the chances for infections and further injury to the animal is multiplied. Amputation of the edematous prolapsed bovine cervix is unacceptable in most instances because amputation of the tissue and organs will, of course, impair the reproductive capabilities of the animal. However, in some instances where the edematous prolapsed bovine cervix goes untreated and where infections occur, amputation is sometimes required.

The accepted technique for treating edematous prolapsed bovine cervix is to attempt to reinsert the cervix into the pelvic canal of the animal. However, in those instances where the cervix is in an extreme edematous condition, it is impossible to reinsert the cervix tissue back into the vagina and into the pelvic canal of the animal. With such a condition, most veterinarians attempt to remove at least some of the fluid that fills the edematous tissue. Most of the methods for removing the fluid from the edematous structure are at best only partially successful.

One of the most widely used methods for reducing the size of an edematous prolapsed bovine cervix in order that the cervix tissue may be reinserted into the pelvic canal is a rather involved procedure wherein sugar is packed around the swollen tissue to osmotically draw the fluids out of the edematous tissue. Various other types of materials have also been suggested for osmotically removing the fluids from such edematous tissue. Such methods involving the osmotic removal of fluid are all time consuming and quite difficult to perform.

Some veterinarians have resorted to a type of hand removal of fluids from the edematous prolapsed bovine cervix tissue by squeezing and "wringing" the fluid from the tissue in order to reduce the size of the cervix to a point where it can be reinserted into the vagina and into the pelvic canal. However, the manual squeezing or wringing of fluid from the swollen tissue very often results in bruising, tearing of the tissue and other injury that endangers the life of the animal if infection sets in.

It is, therefore, recognized that there is a need for an improved type of veterinary appliance that can be utilized to reduce the size of an edematous prolapsed bovine cervix whereby the fluid can be removed from the swollen tissue in a safe, sanitary manner without additional injury to the animal.

SUMMARY OF THE INVENTION

Accordingly, it is an object of this invention to provide an improved veterinary appliance for size reduction of edematous tissue. It is another object of this invention to provide an improved appliance for the size reduction of edematous prolapsed bovine cervix tissue.

Other aspects, objects and advantages of this invention will be apparent to those skilled in the art from the following disclosure and appended claims.

The instant invention is an improved apparatus for use in the size reduction of edematous prolapsed bovine cervix tissue. The apparatus of the invention generally comprises a flexible band member having a first end and a second end with the band member being adapted to fit around the edematous prolapsed bovine cervix tissue. A roller means is rotatably supported by the housing and means are included to operably connect at least one end of the band member to the roller means. When only one end of the band member is operably connected to said roller means, the other end of the band member is affixed to the housing. Means are also included for rotating the roller to thereby decrease the effective length of the band member to thereby exert a constant, even force on the edematous structure to extract fluid therefrom.

DESCRIPTION OF PREFERRED EMBODIMENTS

Figure 1:
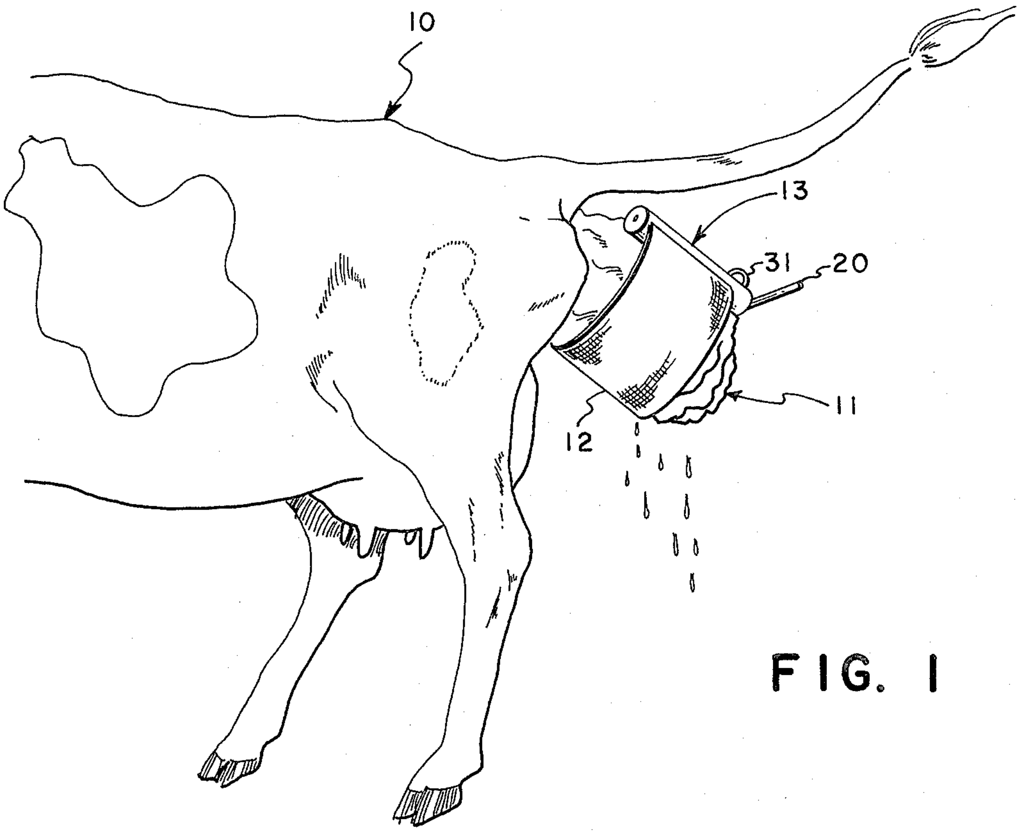
FIG. 1 is a perspective view of the apparatus of the invention showing its function and operation as it is affixed to the edematous prolapsed bovine cervix.
Figure 2:
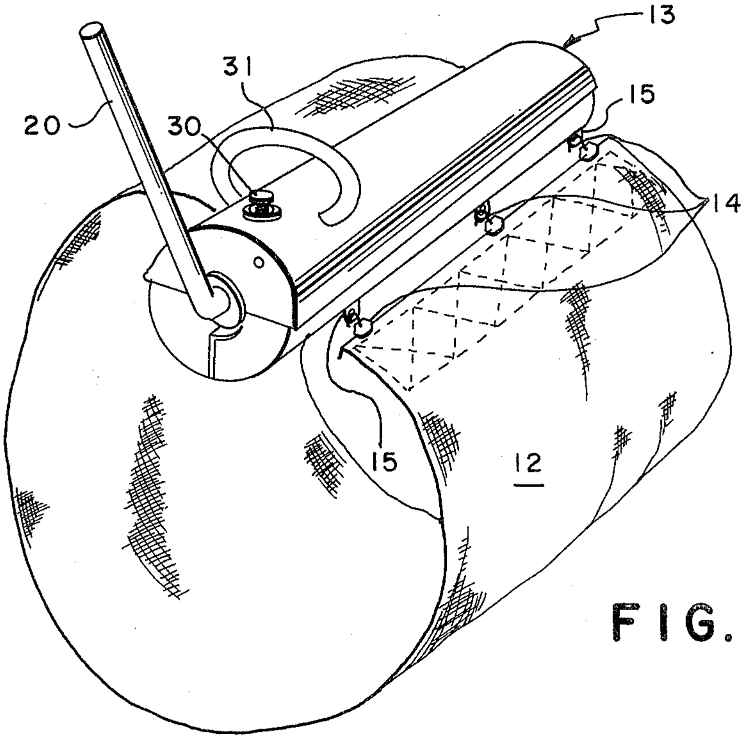
FIG. 2 is a perspective view of one embodiment of the apparatus of this invention.

Some of the preferred embodiments of this invention can best be illustrated by referring to the drawings. FIG. 1 is a perspective illustration of the apparatus of this invention as it is used to reduce the size of an edematous prolapsed bovine cervix. In FIG. 1, female bovine animal 10 is suffering from a condition wherein the cervix and tissue surrounding cervix 11 have been extruded from the vagina of the animal and the extruded material exists in an extreme edematous condition whereby it is swollen to a very large size. As previously mentioned, the edematous prolapsed bovine cervix that has been extruded from inside the animal exists as a spongy, swollen mass of tissue that is filled with a fluid that must be extracted from the tissue prior to reinsertion of the prolapsed bovine cervix into the animal. By using the apparatus of this invention, web member 12 is a relatively broad flexible web having a first end and a second end with the web material being of such size and shape that it can be wrapped around the edematous tissue as illustrated in FIG. 2. Normally, it is preferred that web member 12 be a flexible fabric element that can be wrapped around the extruded edematous tissue without further injury to the tissue. Since the principle of operation of this invention is to literally squeeze the edematous tissue with a constant and evenly distributed squeezing force, it will be appreciated that web member 12 should be relatively flexible and soft whereby it can be wrapped around the edematous tissue. It is preferred that web member 12 be made of some type of fabric such as woven nylon and the like, whereby fluid that is squeezed from the edematous tissue can seep through the fabric.

One end of web member 12 can be adapted to be attached to housing member 13. Housing member 13, as will be described hereinafter, contains various other movable components whereby the effective length of web 12 can be reduced to thereby exert the desired constant and even squeezing on the edematous tissue, as its size is reduced by removal of fluid from the edematous tissue. In the illustrated embodiment, one end of web member 12 is equipped with a plurality of hooks 14 that engage loops 15 which are permanently affixed to housing 13. It will, of course, be appreciated that any convenient method for affixing one end of band member 12 to housing 13 can be utilized. The other end of flexible web or flexible band member 12 is operably connected to a roller means whereby rotation of the roller means will cause the effective length of the band member 12 to be decreased by rotation of the roller means. When the effective length of flexible band member 12 is decreased, the circumference of band member 12, as illustrated in FIG. 2, will decrease to thereby exert a constant and even squeezing force on the edematous tissue as illustrated in FIG. 1. This constant and even squeezing will cause fluid to be squeezed from the edematous tissue to thereby reduce the size of the edematous tissue. Since the tissue is soft and spongy, the fluid contained within the edematous tissue can be squeezed therefrom without rupturing or bruising the tissue.

The apparatus also includes a means for rotating the roller within the housing 13. With the roller means contained within the housing, a suitable slot or opening in the housing walls will allow the flexible band element to be passed through the housing to allow it to operably engage the roller means.

Figure 4:
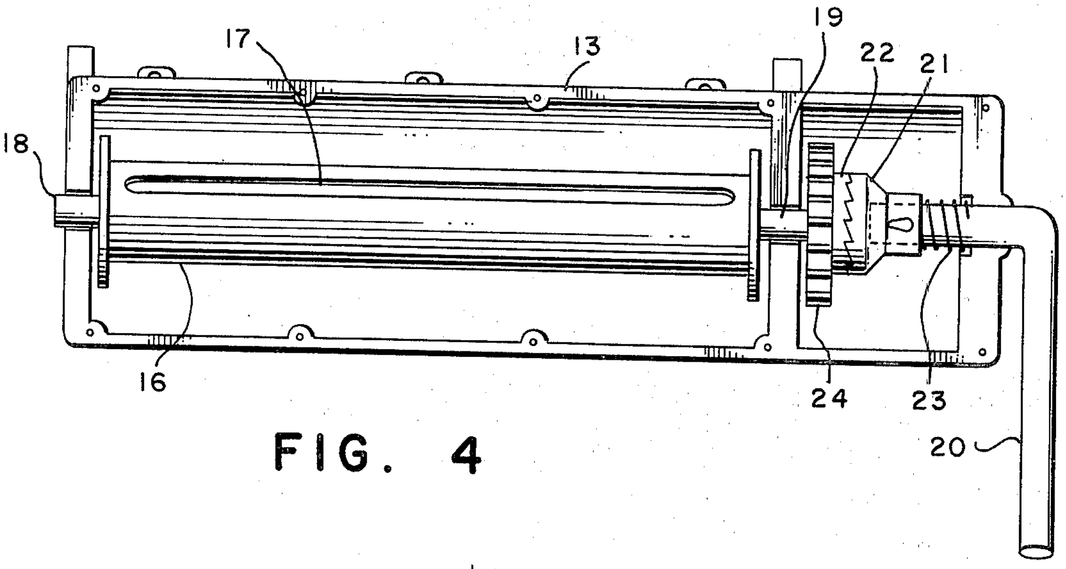
FIG. 4 is a top view of the housing portion of the apparatus of FIG. 3, with the lid removed to expose the internal components of the housing.

FIG. 4 is a top view of housing 13 with the top cover removed to expose roller means 16 which is rotatably supported within housing 13. Roller means 16 is a cylindrical roller that is preferably of a shape and size to receive one end of flexible belt member 12. As illustrated in FIG. 4, roller means 16 is a cylindrical, slotted roller, having a slot 17 disposed along the substantial length of roller 16. The slot is sized to allow the second end of the band member to be inserted into the slot and by rotating the roller in a predetermined direction, flexible band member 12 will be rolled onto the roller to thereby decrease the effective length of the band member. As illustrated, roller 16 is mounted on and supported by suitable axles 18 and 19 which are journaled into bushings within the housing 13 whereby roller 16 is free to rotate upon the application of a suitable force to cause such rotation. Suitable means such as crank handle 20 are operably connected to axle 19 whereby rotation of crank handle 20 in a predetermined direction will also cause rotation of roller 16.

Figure 3:
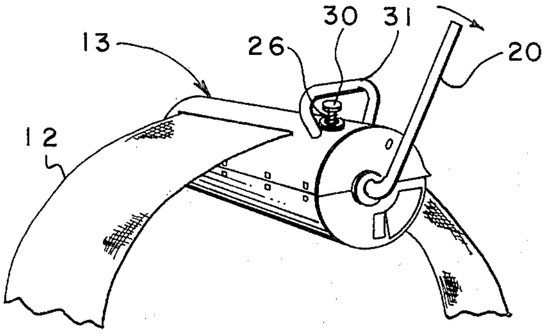
FIG. 3 is a perspective view of a portion of the apparatus of FIG. 2, from the opposite side and showing the arrangement of the flexible band member and means for rotating the roller within the housing.

If desired, crank member 20 can be operably connected to a ratchet assembly that is adapted to cause rotation of the roller means when the crank is rotated in one direction with the crank assembly being allowed to freely rotate in the opposite direction as the roller means is held stationary. As more clearly illustrated in FIG. 4, crank member 20 is operably connected to a first ratchet gear 21 with first ratchet gear 21 being in mating engagement with second ratchet gear 22. Second ratchet gear 22 is rigidly affixed to axle 19 whereby rotation of second ratchet gear 22 will cause rotation of roller means 16. As illustrated in FIG. 4, first ratchet gear 21 is forced into engagement with second ratchet gear 22 by means of ratchet spring 23 which engages a portion of housing 13 and is biased to force the ratchet gears into engagement. Thus, by rotation of crank member 20 in the direction of the arrow, as shown in FIG. 3 (with the lower portion of crank member 20 being moved outwardly from FIG. 4) the ratchet gears will be tightly engaged to thereby cause roller member 16 to rotate in a direction whereby slotted aperture 17 will move in a direction away from the viewer. When roller means 16 is held stationary and the direction of rotation of crank member 20 is reversed (opposite to the arrow shown in FIG. 3) the beveled portions of ratchet gears 21 and 22 will slide across each other and ratchet spring 23 will be slightly compressed to allow crank member 20 to rotate without rotation of roller means 16.

It will be appreciated that any type of suitable means for rotating roller means 16 can be utilized in the instant invention. The double ratchet gear arrangement illustrated in FIG. 4 is only one preferred embodiment. It is not necessary to use such a gear arrangement in all instances. However, such a ratchet arrangement does allow for the apparatus to be used more effectively and easily. In some instances, it may be desirable to include a suitable gear train whereby crank member 20 is affixed to a gear that matingly engages other gears which cause rotation of roller member 16.

Figure 5:
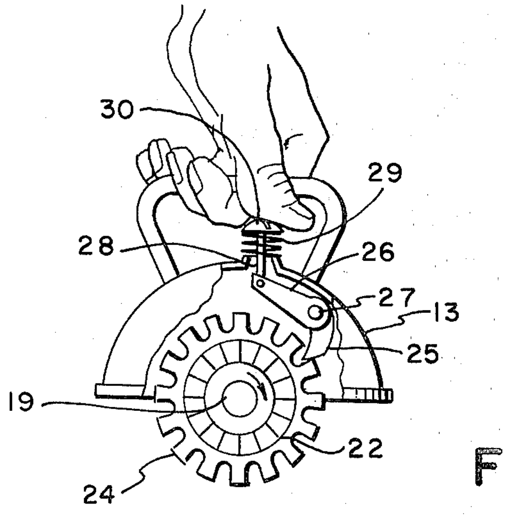
FIG. 5 is an end view of a portion of the housing member of the apparatus of FIG. 3 to illustrate the locking mechanism operably affixed to the roller means.

In the preferred embodiments of this invention, it is desirable to utilize a means to restrict the rotation of the roller whereby the roller means can be locked into place. Thus, by tightening belt member to a predetermined tension, a force will be exerted on the edematous tissue and by locking the roller into position that constant force can be maintained on the edematous tissue without the necessity of manually holding the crank in a predetermined position. As illustrated in FIGS. 4 and 5, locking gear 24 can be affixed to axle 19 whereby restriction or locking in place of locking gear 24 will prevent axle 19 from rotating, thereby also preventing roller means 16 from rotating. As shown in FIG. 5, which is an end view of a portion of the top of housing 13 with a portion of the end cover broken away to expose the gear assembly, locking gear 24 engages locking tongue 25. When locking tongue 25 is swung into position so as to engage the teeth of locking gear 24, locking gear 25 will not rotate. Locking gear 25 can be rigidly affixed to locking lever 26 and the assembly can be pivotally affixed to the interior of housing 13 about pivot pin 27. Thus, when locking gear lever 26 is moved downwardly, it, along with locking tongue 25, will be pivotally rotated about pivot pin 27 whereby locking tongue 25 moves toward the right in FIG. 5, and away from engagement with the teeth of locking gear 24. With locking tongue 25 moved away from the teeth of locking gear 24, crank member 20 can be rotated in the direction indicated by the arrow in FIG. 3 and locking gear 24, which is rigidly affixed to axle 19 will rotate in the direction indicated by the arrow in FIG. 5.

Lock plunger 28 can be utilized to depress to move locking lever 26 downwardly to cause the pivotal rotation of locking tongue 25 away from the teeth of locking gear 24. As illustrated, lock plunger 28 is held upwardly by means of lock plunger spring 29 which is biased to urge lock plunger 28 upwardly and thereby pull locking lever 27 upwardly and to urge locking tongue 25 into engagement with the teeth of locking gear 24. Suitable lock plunger button 30 can be affixed to the upper end of lock plunger 28. Handle 31 can be affixed to housing 13 to assist the operator in affixing the apparatus to the animal to be treated and to facilitate in the operation of the locking mechanism that restricts the rotation of roller 16.

It will be appreciated that while the illustrated apparatus of this invention has been illustrated to provide for a slotted roller to receive one end of flexible band member 12, other methods for operably connecting the band member to roller 16 can also be utilized. Such other means include hooks, clamps, and the like, whereby the free end of band member 12 can be affixed to the roller.

While the foregoing described apparatus has been directed to an apparatus wherein one end of belt member 12 is affixed to housing 13 with the other end being operably connected to roller means 16, it will also be appreciated that both ends of belt member 12 can be operably connected to roller means 16. In such instances, rotation of roller means 16 will also serve to shorten the effective length of belt means 12. Thus, in the broad aspects of this invention, at least one end of belt member 12 will be operably connected to roller means 16. When only one end of belt member 12 is affixed to roller means 16, then the other end of belt member 12 will be affixed to housing 13 by some suitable means as mentioned above.

Figure 3A:
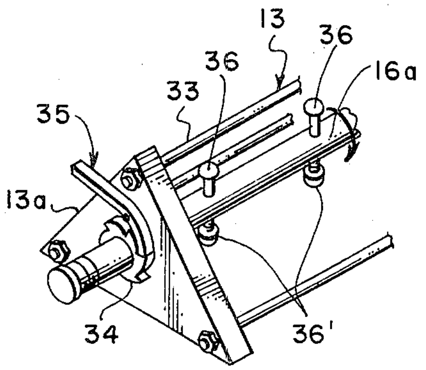
FIG. 3A is a perspective view of a portion of another embodiment of the apparatus of this invention.

In the apparatus illustrated in FIG. 3A, housing 13 is shown as a simplified open housing wherein roller means **16*a* is exposed. Housing 13 in FIG. 3A includes end housing member 13*a* which is suitably equipped with a bushing into which the terminal end of roller 16*a* is journaled with the terminal end extending past the face of housing end member 13*a*. An identical end face plate for housing 13 is disposed on the other end of the housing (not illustrated) into which the other end of roller means 16*a* is journaled and supported for rotation within the housing. Spacer rod 33 engages both of the housing end plates to hold them in proper position. Ratchet gear 34 is rigidly affixed to the end of roller means 16*a* that projects through end pace plate 13*a*. Locking lever or dog 35 is pivotally affixed to end face plate 13*a* and engages ratchet gear 34. If desired, dog 35 can be spring loaded to hold it in contact with ratchet gear 34. Thus, as roller means 16*a* is rotated in the direction of the arrow shown in FIG. 3A, dog 35 will allow such rotation by riding over the beveled portions of ratchet gear 34 but it will prevent roller means 16 from rotating in an opposite direction. Rotation in the opposite direction can be accomplished by pivotally moving dog 35 away from contact with ratchet gear 34 by depressing the upper end of dog 35 to cause it to pivotally rotate away from contact with ratchet gear 34. Rotation of roller means 16*a* in FIG. 3A can be accomplished by cperably connecting a suitable handle means to the terminal end of roller means 16*a*. The handle means can be a simple rod that is inserted into a suitable aperture or bore that can be perpendicular to the axis of roller means 16*a***.

Roller means **16*a* as illustrated in FIG. 3A can be equipped with suitable lugs or pins 36 that project outwardly from the surface of roller means 16*a*. Lugs or pins 36 are adapted to pass through grommets that can be installed in the ends of belt member 12. Thus, by equipping belt member 12 with a series of grommets that can be placed over lugs 36, an easy and efficient method for affixing the ends of belt member 12 to roller means 16*a*** is provided.

The apparatus illustrated in FIG. 3A is a simplified apparatus that has several advantages including simplicity of construction, ease in operation and ease in cleaning and disassembly. After use of the apparatus, the belt member can be very simply removed from the roller means and the entire disassembled apparatus can be conveniently washed and sterilized and dried for subsequent use.

It will be appreciated that while the apparatus illustrated in FIG. 3A provides for both ends of the belt member to be affixed to the roller means for rotation, one end of the belt member can be rigidly affixed to the housing while the other end of the belt member is operably connected to the roller.

In the operation of the illustrated apparatus, the diameter of or the effective length of flexible belt 12 will be increased to such a size that it can be easily placed around and over the edematous tissue to be treated. Thereafter, by suitable rotation of the crank member to cause rotation of the roller within housing 13, the effective length of band member 20 can be decreased to bring an even and steady pressure on the edematous tissue. By applying the constant and even pressure to the edematous tissue, fluid can be extracted from the tissue to reduce the size to a point where it can easily be reinserted into the vagina and the pelvic canal of the animal.

The apparatus, of course, provides for a safe, sanitary method for reducing the size of the edematous tissue.

It will be appreciated that the apparatus can be fabricated from known materials. Thus, flexible band 12 can be fabricated from a strong, durable fabric material and the other components can be fabricated from some suitable metallic, or molded plastic material. By using such durable materials, it is, of course, convenient to clean and sterilize the apparatus to prevent undue infection to the animal being treated.

Various changes and modifications may be made in the foregoing disclosure without departing from the spirit and ycope of this invention.

I claim:

1. An apparatus for the size reduction of an edematous prolapsed bovine cervix which comprises:

(a) a flexible band member having a first end and a second end and adapted to fit around said edematous prolapsed bovine cervix;

(b) a housing member;

(c) a roller means rotatably supported by said housing;

(d) means for operably connecting at least one end of said band member to said roller means;

(e) when only one end of said band member is operably connected to said roller, a means for affixing the other end of said band member to said housing; and (f) means for rotating said roller means to thereby decrease the effective length of said band member.

2. The apparatus of claim 1 wherein said first end of said band member is affixed to said housing and said second end is operably connected to said roller means.

3. The apparatus of claim 1 wherein said housing includes means to controllably restrict rotation of said roller means.

4. The apparatus of claim 3 wherein said means to controllably restrict rotation includes a gear means operably connected to said roller means with a locking tongue engaging said gear means to prevent rotation of said roller means.

5. The apparatus of claim 1 wherein said means for affixing said second end of said band member to said roller means includes a slotted aperture extending along at least a portion of the length of said roller, said slotted aperture being adapted to receive said second end of said band member.

6. The apparatus of claim 1 wherein said means for rotating said roller means includes a crank means operably connected to said roller means.

7. The apparatus of claim 6 wherein said crank means is operably connected to a ratchet assembly adapted to cause rotation of said roller means when said crank means is rotated in one direction.

* * * * *